United States Patent [19]
Jonker

[11] Patent Number: 5,542,940
[45] Date of Patent: Aug. 6, 1996

[54] BIODEGRADABLE DISPOSABLE DIAPER

[76] Inventor: Johannes C. Jonker, Kadoelermeer 53, 3068 KE Rotterdam, Netherlands

[21] Appl. No.: 241,147

[22] Filed: May 10, 1994

[30] Foreign Application Priority Data

May 10, 1993 [NL] Netherlands ............................ 9300789

[51] Int. Cl.$^6$ .............................. A61F 13/15; A61F 13/20
[52] U.S. Cl. ......................... 604/367; 604/358; 604/378; 604/384
[58] Field of Search .................................. 604/358, 365, 604/367, 378, 384, 385.1

[56] References Cited

U.S. PATENT DOCUMENTS

| | | | |
|---|---|---|---|
| 3,663,348 | 5/1972 | Liloia et al. | 604/365 |
| 3,683,917 | 8/1972 | Comerford . | |
| 3,777,758 | 12/1973 | Mesek et al. | 604/365 |
| 3,779,246 | 12/1973 | Mesek et al. | 604/365 |
| 3,939,836 | 2/1976 | Tunc | 604/370 |
| 4,215,692 | 8/1980 | Levesque | 604/374 |
| 5,026,363 | 6/1991 | Pratt . | |
| 5,185,009 | 2/1993 | Sitnam . | |
| 5,207,664 | 5/1993 | Blanco . | |

OTHER PUBLICATIONS

Database WPI, Section PQ, Week 8951, Derwent Publications Ltd., London, GB; Class P32, AN 89–373013 & JP,A,1 277 560 (KAO) 8 Nov. 1989.
Patent Abstracts of Japan, vol. 014, No. 047 (C– 0682) 29 Jan. 1990 & JP,A,01 277 560 (KAO) 8 Nov. 1989.

*Primary Examiner*—David H. Willse
*Assistant Examiner*—P. Zuttarelli
*Attorney, Agent, or Firm*—Curtis, Morris & Safford, P.C.

[57] ABSTRACT

A disposable diaper comprising a liquid permeable bodyside inner liner and an at least substantially liquid impermeable outer layer, which form a front panel and a rear panel, with a liquid-absorbent batt sandwiched between the inner liner and the outer layer, and with elastic leg openings, characterized in that the inner liner and the outer liner are at least substantially made of a cellulosic material of the "wet-strong long fiber" type.

37 Claims, 1 Drawing Sheet

BIODEGRADABLE DISPOSABLE DIAPER

BACKGROUND OF THE INVENTION

The invention relates to a biodegradable disposable diaper provided with a liquid permeable bodyside inner liner and an at least substantially liquid impermeable outer layer, which form a front panel and a rear panel, with a liquid-absorbent batt sandwiched between the inner liner and the outer layer.

It is noted that the term disposable diaper in this context is not only understood to mean a disposable device which is provided on small children's bodies for collecting urine and feces therein, but also a disposable device in particular for incontinent adults.

A disposable diaper is known from International Patent Application No. WO 84/04242 (Johnson & Johnson Products, Inc.). The disposable diaper of International Patent Application No. WO 84/04242 has a synthetic outer layer of polyethylene and a non-woven synthetic inner liner, with a batt of a fluff-like cellulosic material sandwiched therebetween.

A drawback of the known disposable diaper is that it is very environment-unfriendly because of its use of synthetic materials. The production of such a diaper requires the use of materials which are harmful to the environment. The processing into waste of the diaper causes serious harm to the environment. The fact of the matter is that in addition to the fact that the known disposable diapers, which comprise a synthetic outer layer and a synthetic inner liner will lie on a mountain of waste for a considerable period of time, they generate noxious ash remnants plus gases ($CO_2$ emission) upon being incinerated. The problem described herein is certainly not an imaginary one, in view of the enormous scale on which the known disposable diapers are being used. In order to overcome the above-mentioned drawback a so-called "diaper service" has already been proposed. This "diaper service", is based on the distribution of clean cotton diapers of the time-honored type to users who are members of this "diaper service", collecting and cleaning used cotton diapers from such users and subsequently distributing the cleaned, used cotton diapers again, etc. Although the "diaper service" enjoys a growing popularity, a large part of the diaper users have a continued need for disposable diapers.

U.S. Pat. No. 5,207,664 (Blanco) is related to a disposable diaper formed of biodegradable materials, which includes an outer fabric sheet coextensively and adherably mounted to a fibrous underlying sheet, with a fluid absorbing fabric matrix mounted medially of the fibrous sheet and an inner porous sheet mounted coextensively to the fabric matrix web utilizing heat activated adhesive for securement of the layers together. The outer fabric sheet is formed of a natural fiber, such as cotton.

U.S. Pat. No. 3,683,917 (Comerford) is directed to a sanitary towel comprising a cellulosic absorbent core, a cellulosic covering material and a biodegradable, water impervious barrier sheet comprising a water repellent tissue, whereby use is made of a hydrocolloidal material being capable of swelling in body fluids and cooperating with the repellent tissue to form an impervious barrier to body fluids.

U.S. Pat. No. 5,026,363 (Pratt) relates to a flushable diaper comprising, in combination, a three layered combined structure configured as a lightweight, small bikini bottom, having a top layer, a middle layer and a bottom layer. The bottom layer is made of a breathable, hydrophobic material of the kind sold by DuPont under the trademark "EVLON" which consists of 40% polyester fiber and 60% calcium carbonate. The middle layer comprises a wood pulp type material in order to be capable of absorbing a relatively large amount of liquid waste. The top layer is a material selected from at least one of the group consisting of cotton and rayon in order to provide a thin moisture permeable, biodegradable layer.

U.S. Pat. No. 5,185,009 (Sitnam) describes a biodegradable diaper comprising an outer sheet of biodegradable material able to resist water absorption, an inner sheet of biodegradable material able to allow the passage of water and attached to the outer sheet by a biodegradable adhesive at the periphery to form an envelope, a super absorbent core within the envelope, and a water resistant film of biodegradable material located within the core to assist in fluid distribution into the core. The outer sheet is of rayon, whereas the inner sheet is of polyethylene. The biodegradable adhesive is a natural rubber latex, whereby the core may be a sulphite cooked pulp subjected to a hammer mill.

None of the above patent publications discloses or suggests to a person skilled in the art a disposable diaper according to the claims of the present application. None of the disposable diapers proposed according to the above-described U.S. Patents have become a success, either because the materials required by them make the resultant product too expensive, or because they exhibited urine leakage, due to the layers not being strong enough in a wet condition. In particular these drawbacks have been overcome by the proposed disposable diaper according to the present application, which has resulted in resounding commercial success.

OBJECTS OF THE INVENTION

The object of the invention is to provide an environment-friendly disposable diaper, which has excellent diaper properties, especially with respect to absorption, comfort and strength, and which are easy to produce and are attractively priced.

SUMMARY OF THE INVENTION

In order to accomplish this objective the disposable diaper of the present invention includes an inner liner and an outer layer that are at least substantially made of a cellulosic material of the "wet-strong long fiber" type. As a result of this, the disposable diaper as a whole is readily biodegradable and consequently absolutely environment-friendly. The "wet-strong long fiber" paper serves to replace the synthetic "non-woven" inner liner and the polyethylene outer layer of the known disposable diaper. The "wet-strong long fiber" paper is safe for small children, it exhibits great strength in wet condition in comparison with ordinary paper, because of the long fibers from which it is built up, and is very interesting from an economic point of view, since it is cheaper than the aforementioned non-woven material. The term "wet-strong long fiber" paper is a frequently used term in the paper industry, which is used to denote paper having a cellulose fiber length from 10 cm in its natural state.

One embodiment of a disposable diaper according to this invention is characterized in that the cellulosic material contains fibers from plants of at least one species selected from the group consisting of abaca, hemp, kenaf, sisal and jute. It is preferred to use fibers of leaves and/or stems of banana plants of the abaca species for the cellulosic material of the inner liner and the outer layer of the diaper. Because of their average length (1.5–3 meters), strength and flexibility, these fibers are particularly suitable for use in the disposable diaper proposed herein. It is noted in this connection that hemp, kenaf, sisal and jute fibers have an average length varying between 1 and 5 meters.

As a result of this a disposable diaper having optimum diaper properties is obtained, which is readily biodegradable.

A disposable diaper according to the invention is preferably provided with perforations in the liquid permeable inner liner. All this effects a quicker permeation of urine.

Another embodiment of the invention is characterized in that it can be used in combination with overpants at least substantially made of a liquid impermeable material, preferably (knitted) polyester. Such overpants, which are reusable, may serve as an additional protection against any urine leaking through, if desired.

A disposable diaper according to the invention is preferably provided with means (for example adhesive strips) for attaching the disposable diaper around a user's hips.

Another embodiment of the invention is characterized in that the batt contains a fluff-like, cellulosic material.

DESCRIPTION OF A PREFERRED EMBODIMENT

Figure 1:
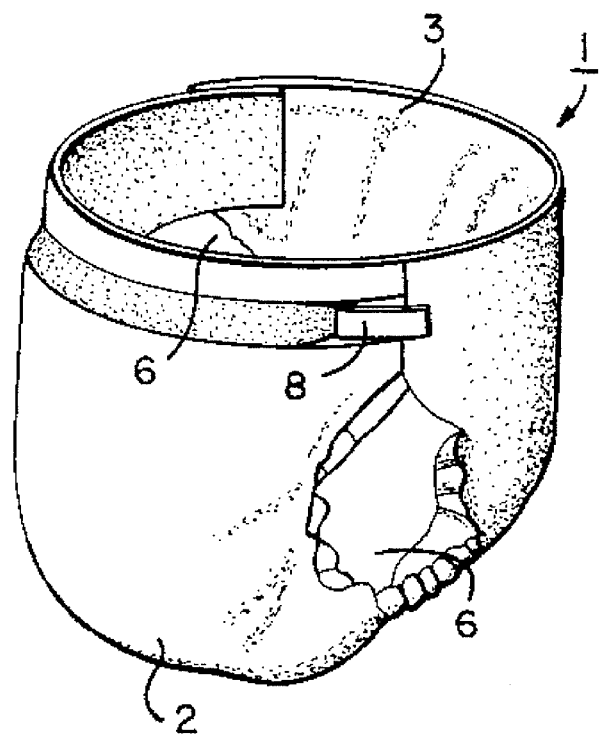
FIG. 1—diagrammatically illustrates a disposable diaper according to the invention in worn condition.
Figure 2:
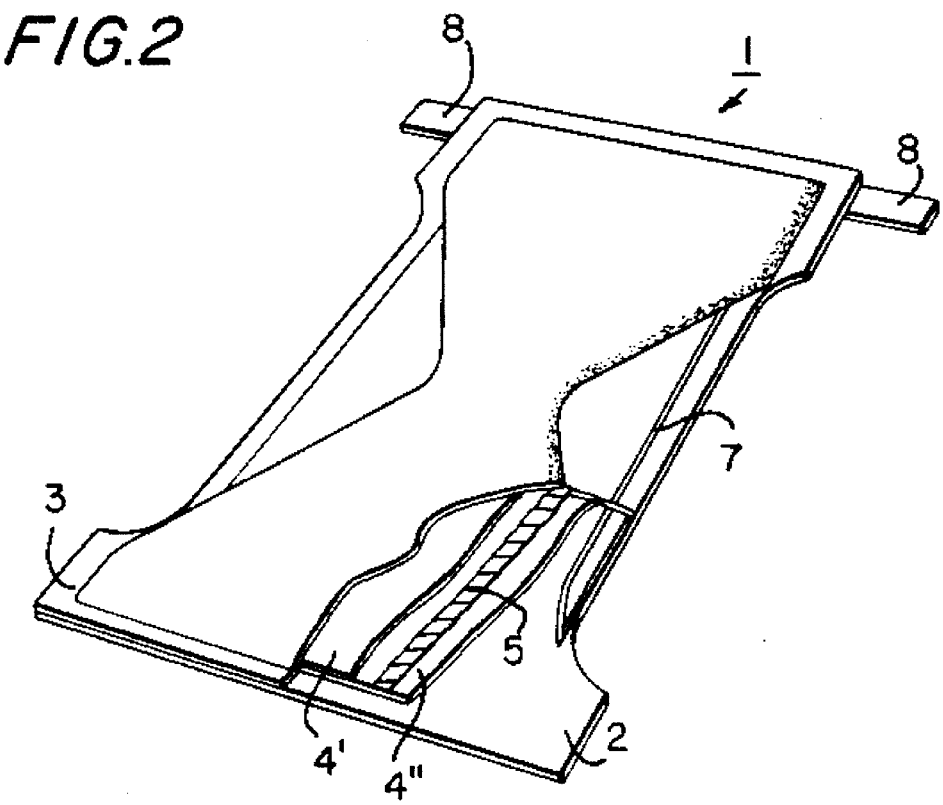
FIG. 2—diagrammatically illustrates the disposable diaper of FIG. 1 in stretched (partially cut-away view).

FIGS. 1 and 2 show a disposable diaper 1 according to the invention, provided with an at least substantially liquid impermeable outer layer 2, a liquid permeable inner liner 3 and an absorbent batt 4 sandwiched therebetween.

The outer layer 2 and the inner liner 3 are made of a cellulosic material, preferably fibers from leaves and/or stems of plants such as abaca, hemp, kenaf, sisal and jute. Preferably the leaves and/or stems of banana plants of the abaca species are used. Because of their length, considerable strength and flexibility these fibers are particularly suitable for use in the disposable diaper according to the invention. In a preferred embodiment the inner liner 3 has at least one of the following properties:

--- surface weight between 13 and 23 g/m$^2$
(preferably 17 g/m$^2$);
surface yield between 43 and 77 m$^2$/kg
(preferably 58 m$^2$/kg);
thickness between 0.050 and 0.080 mm
(preferably 0.063 mm);
tensile strength:
  a) dry, longitudinally >10 N/15 mm
  b) dry, diagonally >3 N/15 mm
  c) wet, diagonally >1 N/15 mm;
degree of whiteness: >75%.

---

In a preferred embodiment the outer layer 2 has at least one of the following properties:

--- surface weight between 20 and 25 g/m$^2$
(preferably 23 g/m$^2$);
surface yield between 40 and 50 m$^2$/kg
(preferably 43 m$^2$/kg);
thickness between 0.060 and 0.080 mm
(preferably 0.072 mm);
tensile strength:

--- a) dry, longitudinally >20 N/15 mm
  b) dry, diagonally >4 N/15 mm
  c) wet, diagonally >1.5 N/15 mm;
degree of whiteness: >75%.

---

This "wet-strong long fiber" paper, from which the outer layer is made, preferably has a strength of 23 g/m$^2$. In another possible embodiment, the inner side of outer layer 2 is provided with a biodegradable coating, to enhance its impermeability.

Batt 4 contains a fluff-like, cellulosic material, and preferably batt 4 consists of two layer portions 4' and 4", provided one on top of the other, with absorbent strips 5 sandwiched therebetween.

The outer layer 2 and the inner liner 3 and the outer layer 2 and the batt 4 are attached together in accordance with known techniques.

The disposable diaper 1 also includes leg openings 6 with elastic strings 7, as well as adhesive strips 8 for attaching the disposable diaper around the body of, for example, a small child.

It is preferred to use overpants preferably made of knitted polyester over the disposable diaper 1 in case additional protection against any urine leakage and the like is desired.

What is claimed is:

1. A disposable diaper comprising means for providing a liquid permeable bodyside inner liner of a substantially cellulosic material of wet-strong long fibers having a wet tensile strength, diagonally, greater than 1N/15 mm, means for providing a substantially liquid impermeable outer layer of a substantially cellulosic material of wet-strong long fibers, having a wet tensile strength, diagonally, greater than 1.5N/15 mm, and a liquid-absorbent batt sandwiched between said inner liner and said outer layer, wherein said cellulosic material comprises said long fibers, having a length from 10 cm in their natural state and coming from at least one plant chosen from the group consisting of abaca, hemp, kenaf, sisal and jute, and wherein the inner liner has a surface weight of about 13 g/m$^2$ to about 23 g/m$^2$.

2. The disposable diaper of claim 1, wherein the inner liner has a surface weight of about 17 g/m$^2$.

3. The disposable diaper of claim 1, wherein said inner liner is provided with perforations.

4. The disposable diaper of claim 1, wherein said diaper is provided with means for attaching said diaper around a user's hips.

5. A disposable diaper comprising means for providing a liquid permeable bodyside inner liner of a substantially cellulosic material of wet-strong long fibers having a wet tensile strength, diagonally, greater than 1N/15 mm, means for providing a substantially liquid impermeable outer layer of a substantially cellulosic material of wet-strong long fibers, having a wet tensile strength, diagonally, greater than 1.5N/15 mm, and a liquid-absorbent batt sandwiched between said inner liner and said outer layer, wherein said cellulosic material comprises said long fibers, having a length from 10 cm in their natural state and coming from at least one plant chosen from the group consisting of abaca, hemp, kenaf, sisal and jute, and wherein the inner liner has a surface yield between about 43 m$^2$/kg and about 77 m$^2$/kg.

6. The disposable diaper of claim 5, wherein the inner liner has a surface yield of about 58 m$^2$/kg.

7. The disposable diaper of claim 5, wherein said inker liner is provided with perforations.

8. The disposable diaper of claim 5, wherein said diaper is provided with means for attaching said diaper around a user's hips.

9. A disposable diaper comprising means for providing a liquid permeable bodyside inner liner of a substantially cellulosic material of wet-strong long fibers, having a wet tensile strength, diagonally, greater than 1N/15 mm, means for providing a substantially liquid impermeable outer layer of a substantially cellulosic material of wet-strong long fibers, having a wet tensile strength, diagonally, greater than 1.5N/15 mm, and a liquid-absorbent batt sandwiched between said inner liner and said outer layer, wherein said cellulosic material comprises said long fibers, having a length from 10 cm in their natural state and coming from at least one plant chosen from the group consisting of abaca, hemp, kenaf, sisal and jute, and wherein the inner liner has a tensile strength of:

a) dry, longitudinally >10N/15 mm;

b) dry, diagonally >3N/15 mm.

10. The disposable diaper of claim 9, wherein said inner liner is provided with perforations.

11. The disposable diaper of claim 9, wherein said diaper is provided with means for attaching said diaper around a user's hips.

12. A disposable diaper comprising means for providing a liquid permeable bodyside inner liner of a substantially cellulosic material of wet-strong long fibers, having a wet tensile strength, diagonally, greater than 1N/15 mm, means for providing a substantially liquid impermeable outer layer of a substantially cellulosic material of wet-strong long fibers, having a wet tensile strength, diagonally, greater than 1.5N/15 mm, and a liquid-absorbent batt sandwiched between said inner liner and said outer layer, wherein said cellulosic material comprises said long fibers, having a length from 10 cm in their natural state and coming from at least one plant chosen from the group consisting of abaca, hemp, kenaf, sisal and jute, and wherein the outer layer has a surface weight of between about 20 and about 25 g/m$^2$.

13. The disposable diaper of claim 12, wherein the outer layer has a surface weight of about 23 g/m$^2$.

14. The disposable diaper of claim 12, wherein said inner liner is provided with perforations.

15. The disposable diaper of claim 12, wherein said diaper is provided with means for attaching said diaper around a user's hips.

16. A disposable diaper comprising means for providing a liquid permeable bodyside inner liner of a substantially cellulosic material of wet-strong long fibers, having a wet tensile strength, diagonally, greater than 1N/15 mm, means for providing a substantially liquid impermeable outer layer of a substantially cellulosic material of wet-strong long fibers, having a wet tensile strength, diagonally, greater than 1.5N/15 mm, and a liquid-absorbent batt sandwiched between said inner liner and said outer layer, wherein said cellulosic material comprises said long fibers, having a length from 10 cm in their natural state and coming from at least one plant chosen from the group consisting of abaca, hemp, kenaf, sisal and jute, and wherein the outer layer has a surface yield of between about 40 and about 50 m$^2$/kg.

17. The disposable diaper of claim 16, wherein the outer layer has a surface weight of about 43 m$^2$/kg.

18. The disposable diaper of claim 16, wherein said inner liner is provided with perforations.

19. The disposable diaper of claim 16, wherein said diaper is provided with means for attaching said diaper around a user's hips.

20. A disposable diaper comprising means for providing a liquid permeable bodyside inner liner of a substantially cellulosic material of wet-strong long fibers, having a wet tensile strength, diagonally, greater than 1N/15 mm, means for providing a substantially liquid impermeable outer layer of a substantially cellulosic material of wet-strong long fibers, having a wet tensile strength, diagonally, greater than 1.5N/15 mm, and a liquid-absorbent batt sandwiched between said inner liner and said outer layer, wherein said cellulosic material comprises said long fibers, having a length from 10 cm in their natural state and coming from at least one plant chosen from the group consisting of abaca, hemp, kenaf, sisal and jute, and wherein the outer layer has a tensile strength of:

a) dry, longitudinally >20N/15 mm;

b) dry, diagonally >4N/15 mm.

21. The disposable diaper of claim 20, wherein the outer layer has a degree of whiteness greater than about 75%.

22. The disposable diaper of claim 20, wherein said inner liner is provided with perforations.

23. The disposable diaper of claim 20, wherein said diaper is provided with means for attaching said diaper around a user's hips.

24. A disposable diaper comprising means for providing a liquid permeable bodyside inner liner of a substantially cellulosic material of wet-strong long fibers, having a wet tensile strength, diagonally, greater than 1N/15 mm, means for providing a substantially liquid impermeable outer layer of a substantially cellulosic material of wet-strong long fibers, having a wet tensile strength, diagonally, greater than 1.5N/15 mm, and a liquid-absorbent batt sandwiched between said inner liner and said outer layer, wherein said cellulosic material comprises said long fibers, having a length from 10 cm in their natural state and coming from at least one plant chosen from the group consisting of abaca, kenaf and sisal, and wherein the inner liner has a thickness between about 0.050 and about 0.080 mm.

25. The disposable diaper of claim 24, wherein the inner liner has a thickness of about 0.063 mm.

26. The disposable diaper of claim 24, wherein said inner liner is provided with perforations.

27. The disposable diaper of claim 24, wherein said diaper is provided with means for attaching said diaper around a user's hips.

28. A disposable diaper comprising means for providing a liquid permeable bodyside inner liner of a substantially cellulosic material of wet-strong long fibers, having a wet tensile strength, diagonally, greater than 1N/15 mm, means for providing a substantially liquid impermeable outer layer of a substantially cellulosic material of wet-strong long fibers, having a wet tensile strength, diagonally, greater than 1.5N/15 mm, and a liquid-absorbent batt sandwiched between said inner liner and said outer layer, wherein said cellulosic material comprises said long fibers, having a length from 10 cm in their natural state and coming from at least one plant chosen from the group consisting of abaca, kenaf and sisal, and wherein the inner liner has a degree of whiteness greater than about 75%.

29. The disposable diaper of claim 28, wherein said inner liner is provided with perforations.

30. The disposable diaper of claim 28, wherein said diaper is provided with means for attaching said diaper around a user's hips.

31. A disposable diaper comprising means for providing a liquid permeable bodyside inner liner of a substantially cellulosic material of wet-strong long fibers, having a wet tensile strength, diagonally, greater than 1N/15 mm, means for providing a substantially liquid impermeable outer layer of a substantially cellulosic material of wet-strong long fibers, having a wet tensile strength, diagonally, greater than 1.5N/15 mm, and a liquid-absorbent batt sandwiched between said inner liner and said outer layer, wherein said cellulosic material comprises said long fibers, having a length from 10 cm in their natural state and coming from at least one plant chosen from the group consisting of abaca, kenaf and sisal, and wherein the outer layer has a thickness between about 0.060 and about 0.080 mm.

32. The disposable diaper of claim 31, wherein the outer layer has a thickness of about 0.072 mm.

33. The disposable diaper of claim 31, wherein said inner liner is provided with perforations.

34. The disposable diaper of claim 31, wherein said diaper is provided with means for attaching said diaper around a user's hips.

35. A disposable diaper comprising means for providing a liquid permeable bodyside inner liner of a substantially cellulosic material of wet-strong long fibers, having a wet tensile strength, diagonally, greater than 1N/15 mm, means for providing a substantially liquid impermeable outer layer of a substantially cellulosic material of wet-strong long fibers, having a wet tensile strength, diagonally, greater than 1.5N/15 mm and a liquid-absorbent batt sandwiched between said inner liner and said outer layer, wherein said cellulosic material comprises said long fibers, having a length from 10 cm in their natural state and coming from at least one plant chosen from the group consisting of abaca, kenaf and sisal, and wherein the batt comprises a fluff-like cellulosic material.

36. The disposable diaper of claim 35, wherein said inner liner is provided with perforations.

37. The disposable diaper of claim 35, wherein said diaper is provided with means for attaching said diaper around a user's hips.

* * * * *